(12) United States Patent
Duncavage et al.

(10) Patent No.: US 7,235,099 B1
(45) Date of Patent: Jun. 26, 2007

(54) SPHENOID SINUS STENT

(75) Inventors: James Duncavage, Brentwood, TN (US); Jon E. Hoogenakker, Inver Grove Heights, MN (US); Bradley D. Robb, Maple Plain, MN (US)

(73) Assignee: Micromedics, Inc., St. Paul, MN (US)

( * ) Notice: Subject to any disclaimer, the term of this patent is extended or adjusted under 35 U.S.C. 154(b) by 310 days.

(21) Appl. No.: 11/012,933

(22) Filed: Dec. 14, 2004

(51) Int. Cl.
*A61F 2/06* (2006.01)

(52) U.S. Cl. ............................ 623/1.15; 623/23.7
(58) Field of Classification Search ............... 623/10, 623/1.11–1.16; 606/155
See application file for complete search history.

(56) References Cited

U.S. PATENT DOCUMENTS

| | | | |
|---|---|---|---|
| 4,674,506 A * | 6/1987 | Alcond | 606/153 |
| 5,425,739 A * | 6/1995 | Jessen | 606/155 |
| 6,027,510 A * | 2/2000 | Alt | 606/108 |
| 2004/0148032 A1* | 7/2004 | Rutter et al. | 623/23.7 |
| 2005/0048121 A1* | 3/2005 | East et al. | 424/486 |
| 2005/0137614 A1* | 6/2005 | Porter et al. | 606/153 |
| 2006/0036313 A1* | 2/2006 | Vassiliades | 623/1.23 |

* cited by examiner

*Primary Examiner*—Suzette Gherbi
(74) *Attorney, Agent, or Firm*—Merchant & Gould P.C.

(57) ABSTRACT

A stent specifically designed for use in treating chronic sphenoid sinusitis comprises a soft compressible plastic tube of a predetermined diameter having a proximal end, a distal end and a lumen extending therebetween. The stent has a generally hemispherical hollow dome integrally molded to its distal end. The diameter of the dome is greater than the predetermined diameter of the plastic tube. The stent further includes an integrally molded annular flange located a short predetermined distance proximal to the hemispherical dome. The device is designed to be fitted through a surgically enlarged ostium of the sphenoid sinus such that the dome resides within the sinus cavity and the flange abuts the bony wall surrounding the ostium. The stent maintains the ostium patent and permits irrigation/suctioning via the stent's lumen.

8 Claims, 3 Drawing Sheets

SPHENOID SINUS STENT

BACKGROUND OF THE INVENTION

I. Field of the Invention

This invention relates generally to stents for maintaining a passageway in an animal body patent, and more particularly to a stent specifically designed for use in treating chronic sinusitis where the sphenoid sinus is involved.

II. Discussion of the Prior Art

The paranasal sinuses are air-filled pockets located within the bones of the face and around the nasal cavity. Each sinus is named for the bone in which it is located, e.g., maxillary, ethmoid, frontal and sphenoid.

Each of these air-filled pockets has an opening that connects to the nose. This opening is called an ostium.

The nose and sinuses are closely related. The nasal septum divides the nose into two nasal cavities. The sidewall of the nose (the lateral nasal wall) has three important structures, which are known as the superior, middle and inferior turbinates sometimes referred to as nasal concha. Each is a rounded projection that extends the length of the nasal cavity. The space between each turbinate is called a meatus. Each meatus is named for the turbinate above it.

The inferior turbinate, which is larger than the other turbinates, runs parallel to the floor of the nose. The nasal nasolacrimal duct drains tears into the inferior meatus.

The middle turbinate is located above the inferior turbinate. The anterior or front ethmoid cells open into the middle meatus. The frontal sinus drains into the middle meatus.

The superior turbinate, which is the smallest turbinate, is above the middle turbinate. The posterior ethmoid cells drain into the superior meatus. The space between the superior turbinate, the septum and the sphenoid sinus front wall is known as the sphenoethmoid recess. The sphenoid sinus drains into this recess.

The paranasal sinuses are covered with a special lining or epithelium. The lining secretes mucous, a complex substance that keeps the nose and sinuses moist. The sinus epithelium is ciliated; that is, each cell on its surface has a cilium, which is a relatively long structure that has the capacity to push sinus mucous. This movement of mucous called mucociliary clearance is not random, but rather it is programmed so that the mucous moves along in a specific pattern.

The mucous membranes lining the nasal cavity and the paranasal sinuses may become inflamed due to infections, such as the common cold or allergies. When inflamed, the blood vessel dilates, the membranes swell and the mucous secretions increase. The resulting congestion interferes with breathing and often causes a "runny nose". The infection may spread into the mucous membranes of the paranasal sinuses, blocking their connection with the nasal cavity and causing them to fill with mucous. Since the sinuses act as resonance chambers, this changes the sound of the voice and may also cause such a pressure increase within the sinuses that severe headaches result.

Chronic sinusitis is arbitrary defined as rhinosinusitis of at least 12 consecutive weeks duration and persistence of one major and two minor signs and/or symptoms. Major signs and symptoms include fever, facial pain or pressure, nasal obstruction or nasal discharge with purulence and hyposmia. Cough, dental pain, headache and ear pain or ear fullness are considered minor signs and symptoms. The sphenoid sinus normally drains through its ostium into the space between the superior and middle turbinates. However, due to infection or possibly other causes, the membranes proximate the ostium may swell to the point where drainage ceases and fluid pressure builds up creating severe pain behind the eyes. In treating chronic sphenoid sinusitis, under endoscopic guidance, the ostium of the sphenoid sinus is surgically enlarged to facilitate drainage from the sphenoid sinus cavity. However, tissue swelling and surgical exudates at the surgical site may narrow or scar tissue may close the ostium. Thus a need exists for a means whereby the surgically created opening will remain patent for a period of time sufficient to treat the sinusitis condition.

SUMMARY OF THE INVENTION

In accordance with the present invention, there is provided a stent for placement in the surgically enlarged ostium of sphenoid sinus that comprises a soft, compressible, plastic tube of a predetermined diameter, the tube having a proximal end, a distal end and a lumen extending therebetween. The distal end of the tube terminates in a generally hemispherical, hollow dome whose diameter is greater than the predetermined diameter of the plastic tube. The stent of the present invention further includes an annular flange that extends radially outward from an exterior surface of the compressible plastic tube at a location between the proximal and distal ends of the plastic tube.

In use, the ostium of the sphenoid sinus is surgically enlarged using endoscopic visualization and the stent is then placed into the enlarged ostium. The stent may be placed using a straight Blakesly cup forceps and, in doing so, the hemispherical hollow dome is pinched, allowing it to be compressed for insert through the ostium so that the dome will reside within the sphenoid sinus. The flange or collar remains exterior to the sinus and abuts the bony wall through which the ostium extends. This prevents the stent from falling into the sinus. The hemispherical hollow dome prevents the stent from dislodging out of the sphenoid into the nasal cavity.

Using the lumen of the stent provides access to the sphenoid sinus for irrigating with antibiotics if necessary and suctioning. The surgeon may use the portion of the stent that projects out of the sphenoid sinus as the irrigation and aspiration port.

At a later time, the stent may be removed by again using a forceps to grasp the proximal end of the tube and pulling same in the anterior direction. This causes the front dome to compress on itself and easily pass back through the ostium.

DESCRIPTION OF THE DRAWINGS

Further features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
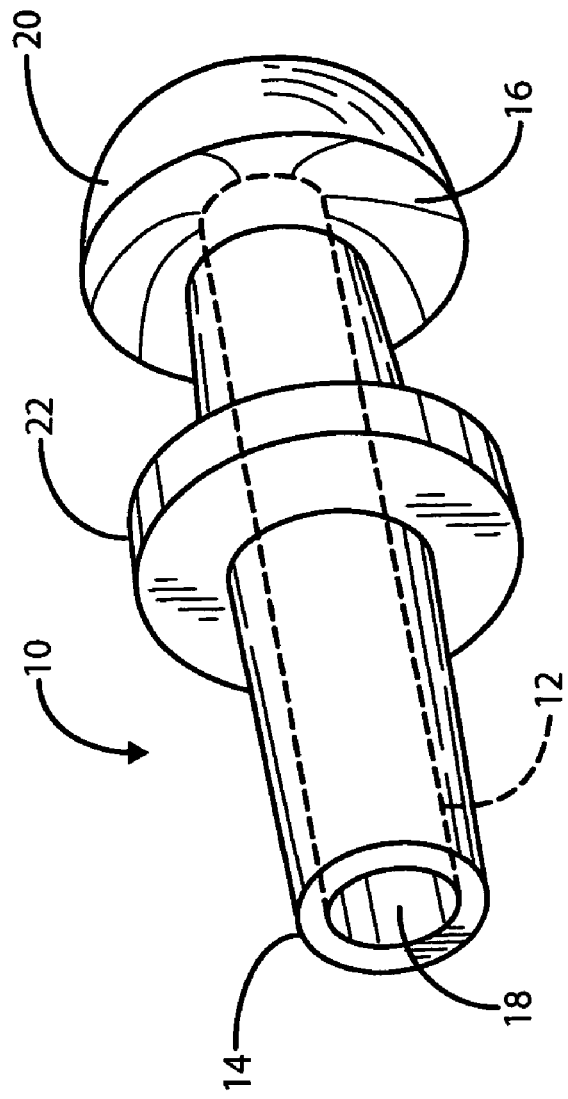
FIG. 1 is a perspective view of the sphenoid sinus stent of the present invention.

Referring first to FIG. 1, there is shown a isometric view of a stent especially designed for placement in the ostium of the sphenoid sinus in the treatment of sphenoid sinusitis. It is indicated generally by numeral 10 and comprises a soft compressible plastic tube 12 of a predetermined outer diameter and having a proximal end 14, a distal end 16 and a lumen 18 extending therebetween. A distal end portion of the tube 12 is tapered and terminates in a integrally formed, generally hemispherical hollow dome 20 whose diameter is greater than the predetermined diameter of the plastic tube 12. The lumen 18 extends all the way through the surface of the dome 20.

A short predetermined distance proximal of the distal end 16 of the tube 12 is an integrally formed, radially extending flange 22, the diameter of which is generally equal to the diameter of the hemispherical dome 20. The stent is preferably formed in a molding operation from a suitable plastic. Without limitation, the plastic may be silicone rubber of a hardness in a range of from about 50 to 70 Shore A.

Figure 3:
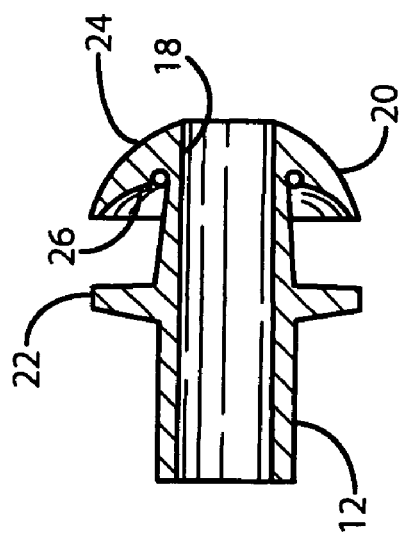
FIG. 3 is a cross-sectional view taken along the line 3—3 in FIG. 2.
Figure 2:
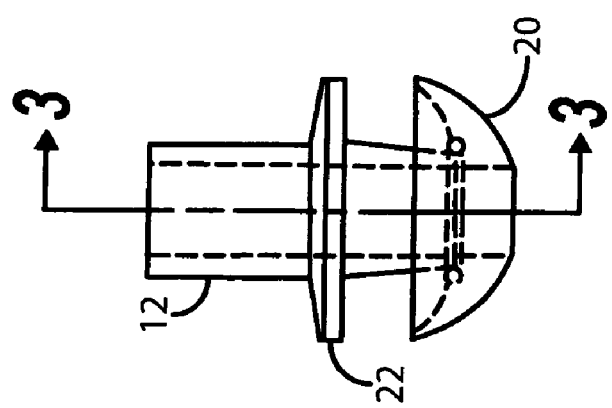
FIG. 2 is a side elevation view thereof.

Referring to the cross-sectional view of FIG. 3 which is taken along the line 3—3 in FIG. 2, the dome 20 has a convex outer wall 24 and a concave inner wall 26. This facilitates the ability to compress the dome to a smaller diameter by pinching the outer periphery of the dome between the jaws of a suitable forceps.

In order to provide an enabling disclosure of a preferred embodiment, the following dimensions may apply to the stent. It should be understood, however, that the values provided are not to be considered as limitive of the invention since the stent device will remain workable with minor changes in the values provided.

| | |
|---|---|
| Length | 0.422 inch |
| Outside Diameter | 0.158 inch |
| Inside Diameter | 0.108 inch |
| Diameter of Flange 22 | 0.315 inch |
| Diameter of Dome 20 | 0.311 inch |
| Radius of Dome | 0.164 inch |
| Gap Between Dome & Flange | 0.079 inch |
| Flange Thickness | 0.028 inch |
| Angle of Taper | 6° |

Figure 4:
FIG. 4 is an anatomical drawing showing placement of the stent through the ostium of the sphenoid sinus.

Referring next to FIG. 4, it is an anatomical sagital view showing the sphenoid sinus 28 with the stent 10 of the present invention inserted through a surgically enlarged ostium, such that the hemispherical head portion 20 resides in the sphenoid sinus 28 while the flange 22 and the proximal portion of the tubular body 12 resides in the sphenoethmoid recess 29 above the superior nasal concha 30. For reference purposes, the middle nasal concha is identified by numeral 32 and the inferior nasal concha by numeral 34 in the view of FIG. 4.

It can be seen that the flange 22 on the stent 10 is of a diameter larger than the surgically enlarged ostium in which the stent 10 is placed. This flange prevents the stent from falling into the sphenoid sinus cavity 28.

As previously indicated, because of the inclusion of the lumen in the stent 10, a surgeon may inject fluids through the lumen into the sphenoid sinus or, alternatively, he/she may suction out the contents of the sinus by coupling a suitable length of tubing from the proximal end of the stent where the tubing then extends out through the external nares 36 of the patient's nose to a source of irrigation fluid or a vacuum.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A stent for placement in a surgically enlarged ostium of a sphenoid sinus in the treatment of sphenoid sinusitis comprising a soft, compressible plastic tube of a predetermined diameter having a proximal end, a distal end and a lumen extending therebetween, said distal end having a rounded dome of a diameter larger than said predetermined diameter of the plastic tube, an outer convex surface and an inner concave surface and with an annular flange integrally formed on an outer diameter of the plastic tube at a location between the proximal and distal ends.

2. The stent as in claim 1 wherein the distance between the annular flange and the distal end is about equal to the thickness of the bone tissue defining the ostium of the sphenoid sinus.

3. The stent as in either claim 1 or claim 2 where the plastic is silicone rubber having a hardness in a range of from 50 to 70 Shore A.

4. The stent as in either claim 1 or claim 2 where the plastic is silicone rubber having a hardness of 60 Shore A.

5. The stent as in either claim 1 or claim 2 wherein the diameter of the rounded dome at the distal end projects radially outward beyond an outer diameter of the plastic tube by an amount generally corresponding to an outer diameter of the annular flange.

6. The stent as in claim 5 wherein the outer diameter of the plastic tube is about 0.158 inch and the outer diameter of the annular flange is about 0.315 inch.

7. A stent for placement in a surgically enlarged ostium of a sphenoid sinus comprising: a soft compressible plastic tube of a predetermined diameter having a proximal end, a distal end and a lumen extending therebetween, said distal end terminating in a generally hemispherical hollow dome having a diameter greater than said predetermined diameter of the plastic tube, and an annular flange extending radially outward from an exterior surface of the plastic tube at a location between said proximal and distal ends of the plastic tube.

8. A method of treating chronic sphenoid sinusitis comprising the steps of:
  (a) surgically enlarging the ostium of the sphenoid sinus;
  (b) inserting the stent of claim 7 into the enlarged ostium such that the hemispherical dome is resident in the sphenoid sinus and the annular flange abuts.

* * * * *